United States Patent
Rathjen

(10) Patent No.: US 10,500,093 B2
(45) Date of Patent: Dec. 10, 2019

(54) DEVICE FOR TREATING EYE TISSUE

(71) Applicant: Christian Rathjen, Bremen (DE)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 1088 days.

(21) Appl. No.: 13/869,534

(22) Filed: Apr. 24, 2013

(65) Prior Publication Data

US 2013/0310816 A1 Nov. 21, 2013

Related U.S. Application Data

(60) Provisional application No. 61/646,484, filed on May 14, 2012.

(51) Int. Cl.
*A61F 9/008* (2006.01)

(52) U.S. Cl.
CPC .... *A61F 9/008* (2013.01); *A61F 2009/00844* (2013.01); *A61F 2009/00872* (2013.01)

(58) Field of Classification Search
None
See application file for complete search history.

(56) References Cited

U.S. PATENT DOCUMENTS

| | | | | |
|---|---|---|---|---|
| 6,607,527 B1* | 8/2003 | Ruiz | ...... | A61F 9/008 351/212 |
| 2009/0171327 A1* | 7/2009 | Kurtz | ...... | A61F 9/008 606/6 |
| 2010/0014051 A1* | 1/2010 | Rathjen | ...... | A61B 3/1005 351/206 |
| 2010/0049175 A1* | 2/2010 | Rathjen | ...... | A61F 9/008 606/5 |

\* cited by examiner

*Primary Examiner* — William J Levicky
*Assistant Examiner* — Shirley X Jian
(74) *Attorney, Agent, or Firm* — Banner & Witcoff, Ltd.

(57) ABSTRACT

An ophthalmic device for treating eye tissue comprises a light source for generating laser pulses, a light projector for focused projection of the laser pulses into the eye tissue and an interferometric measurement system for measuring eye structures. The ophthalmic device comprises an optical element which is movable in relation to the light source and provided for preventing a change in the path length difference between measurement and reference arms of the interferometric measurement system resulting from a change in the length of the light-transmission path caused by a movement of the light projector relative to the light source. The interferometric measurement system enables a flexible measurement of the eye structures before, during and after the treatment, wherein measurement errors in the interferometric measurement system resulting from length changes in the light-transmission path are avoided, which are caused by movements of the light projector relative to the light source.

12 Claims, 5 Drawing Sheets

DEVICE FOR TREATING EYE TISSUE

CROSS-REFERENCE TO RELATED APPLICATIONS

This application claims priority of U.S. Provisional Application No. 61/646,484, filed May 14, 2012, the contents of which are incorporated herein by reference into the present application.

TECHNICAL FIELD

The present invention relates to an ophthalmic device for treating eye tissue by means of laser pulses. In particular, the present invention relates to an ophthalmic device for treating eye tissue, which comprises a light source for generating the laser pulses and a light projector for focused projection of the laser pulses into the eye tissue.

PRIOR ART

Refractive errors such as myopia (nearsightedness), hyperopia (farsightedness or longsightedness) or astigmatism can be corrected permanently these days by refractive surgical treatment. Refractive surgical treatments are surgical interventions on the eye, which change the optical refractive power of the eye with the goal of approximating a desired value of said refractive power to the best possible extent. One of the most important methods in refractive surgery is the so-called laser in-situ keratomileusis (LASIK), in which the inside of the cornea is removed by means of an excimer laser after a corneal flap was previously partially severed and folded away. Such corneal flaps are cut by mechanical microkeratomes or by means of strongly focused femtosecond laser pulses. Suitable femtosecond laser systems generate laser pulses with pulse widths of typically 100 fs to 1000 fs (1 fs=$10^{-15}$ s).

EP 1 731 120 describes a system for cutting a corneal flap by means of femtosecond laser pulses, said system comprising a base station in which the light source for generating the femtosecond laser pulses is arranged. The device comprises a light projector, which is arranged in an application head which is flexibly attached to the base station by an articulated mirror arm and enables a manual application of the application head and light projector onto the eye of a patient. In order to enable the weight of the application head for the manual application by means of the articulated mirror arm, the light projector has smaller dimensioned and therefore lighter dimensioned lens systems compared to the aforementioned systems. In order, despite the smaller dimensioned lens system for cutting the tissue flap nevertheless to be able to process an extended processing area on the eye with focused laser pulses, the application head moreover comprises movement drivers for displacing the light projector in a plurality of processing directions. When the light projector is displaced, the position thereof in relation to the light source is changed in such a way that the length of the light-transmission path from the light source to the light projector is changed.

DESCRIPTION OF THE INVENTION

It is an object of the present invention to propose an ophthalmic device for treating eye tissue by means of laser pulses, which device does not have at least some of the disadvantages of known devices. In particular, it is an object of the present invention to propose an ophthalmic device for treating eye tissue by means of laser pulses, which device enables a simplification of the treatment.

In accordance with the present invention, these objects are achieved by the features of the independent claims. Moreover, further advantageous embodiments emerge from the dependent claims and the description.

An ophthalmic device for treating eye tissue by means of laser pulses comprises a light source for generating the laser pulses and a light projector for focused projection of the laser pulses into the eye tissue, wherein the light projector is movable in relation to the aforementioned light source in such a way that the length of the light-transmission path from the light source to the light projector is changeable.

In particular, the aforementioned objects are achieved by the present invention by virtue of the fact that the ophthalmic device moreover comprises an interferometric measurement system for measuring eye structures. The interferometric measurement system enables flexible measuring of the eye structures, without, to this end, the ophthalmic device for treating the eye tissue having to be moved away from the patient and a measurement device having to be applied in its place. The flexible measurement of the eye structures enabled thereby simplifies the treatment by virtue of the fact that current measurement data of the eye structures can be captured and provided easily and efficiently before the treatment, during the treatment and after the treatment.

In one embodiment variant, the interferometric measurement system is coupled into the aforementioned light-transmission path. Coupling the interferometric measurement system into the light-transmission path from the light source to the light projector enables a measurement of the eye structures at and from the same position, from which and at which the laser pulses for treating the eye tissue are also projected.

The ophthalmic device preferably comprises an optical element, which is movable in relation to the aforementioned light source and provided for preventing a change in the path length difference between measurement arm and reference arm of the interferometric measurement system as a result of a change in the length of the light-transmission path caused by a movement of the light projector. As a result, it is possible to avoid measurement errors in the interferometric measurement system as a result of length changes of the light-transmission path, which measurement errors are caused by movements of the light projector in relation to the light source.

In one embodiment variant, the movable optical element is a mirror arranged in the reference arm and the ophthalmic device comprises a control module and a movement driver, which are configured to displace the mirror in such a way that the path length of the reference arm is adapted in accordance with a change in the length of the light-transmission path caused by a movement of the light projector.

In one embodiment variant, the movable optical element is an optical waveguide coupling, which is fixedly connected to the light projector and which incorporates the light projector into the interferometric measurement system by means of a flexible optical fibre.

In one embodiment variant, the movable optical element is a beam splitter, which is fixedly connected to the light projector and by means of which the measurement arm and the reference arm of the interferometric measurement system are coupled.

In one embodiment variant, the ophthalmic device comprises a further light projector, which is fixedly connected to the light projector and which is incorporated into the interferometric measurement system by means of a flexible optical waveguide.

In one embodiment variant, the ophthalmic device comprises an application head which can be applied onto the eye and the light projector is arranged in the application head. In one variant, the reference arm of the interferometric measurement system is arranged in the application head. In one variant, the interferometric measurement system comprises a light source, which is arranged in the application head. In one variant, the interferometric measurement system comprises a detector, which is arranged in the application head. In an alternative variant, the interferometric measurement system comprises a detector, which is arranged outside of the application head.

In one embodiment variant, the ophthalmic device comprises a base station, the light source for generating the laser pulses is fixedly arranged in the base station, the light projector is connected to the base station via an arm and the reference arm of the interferometric measurement system is arranged in the base station. In one variant, the interferometric measurement system comprises a light source, which is arranged in the base station. In one variant, the interferometric measurement system comprises a detector, which is arranged in the base station.

In one embodiment variant, the interferometric measurement system has a reference arm with a changeable reference arm length.

BRIEF DESCRIPTION OF THE DRAWINGS

In the following text, an embodiment of the present invention is described on the basis of an example. The exemplary embodiment is illustrated by the following attached figures.

WAYS OF IMPLEMENTING THE INVENTION

Figure 1:
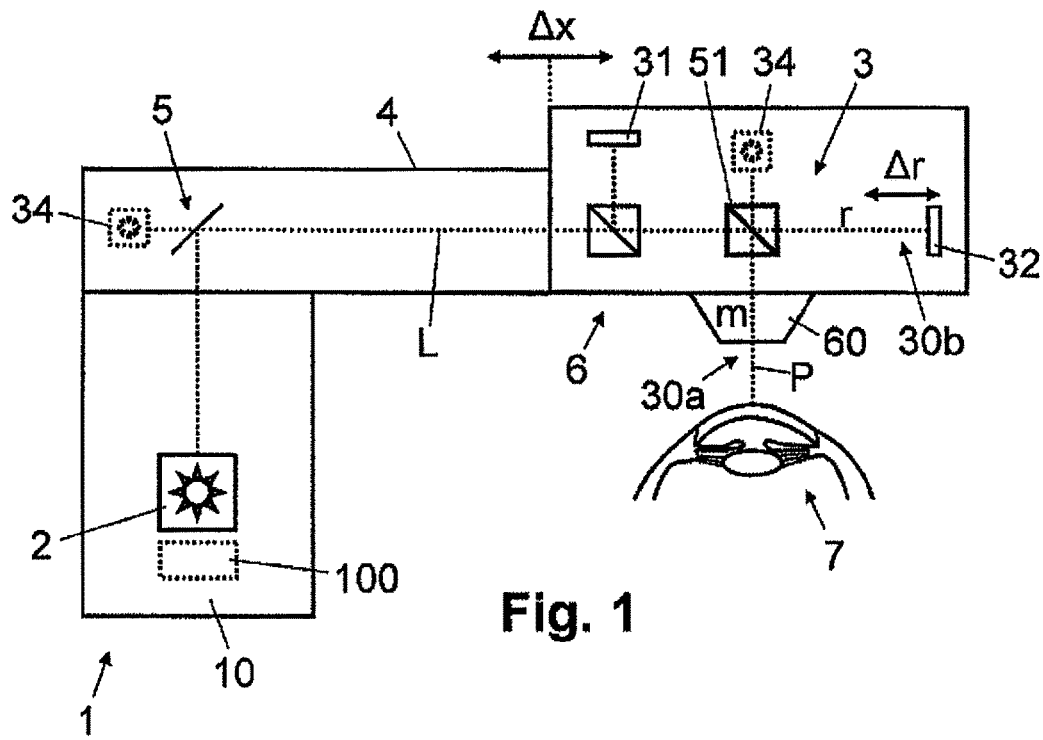
FIG. 1: schematically shows a cross section of an ophthalmic device for treating eye tissue by means of laser pulses, which has an interferometric measurement system for measuring eye structures, which measurement system is arranged in a movable application head.

In FIGS. 1 to 9, the reference sign 1 relates to an ophthalmic device for treating eye tissue 7 by means of laser pulses P. As illustrated schematically in FIGS. 1 to 8, the ophthalmic device 1 comprises a light source 2 for generating the laser pulses P and a light projector 60 for focused projection of the laser pulses P into the eye tissue 7. By way of example, the light source 2 is a laser source for generating a pulsed laser beam with femtosecond laser pulses. The laser pulses P (femtosecond laser pulses) are transmitted along a light-transmission path L from the light source 2 to the light projector 60 by means of an optical transmission system 5. The optical transmission system 5 comprises one or more beam-deflecting scanners (respectively equipped with tiltable/rotatable mirrors), but these are not discussed in more detail here.

As illustrated in FIGS. 1 to 8, the light projector 60 is arranged in an application head 6. The ophthalmic device 1 moreover comprises a base station 10, to which the application head 6 is attached by means of an arm 4. Depending on the embodiment variant, the arm 4 is embodied as a flexible articulated mirror arm or as support arm, which is rigid per se. In the embodiment variants in which the arm 4 is designed as a flexible articulated mirror arm, the application head 6 can be placed manually onto the eye and can be fixed on the eye by means of attachment means 61, which are illustrated schematically in FIGS. 2 and 4. By way of example, the attachment means 61 comprise a suction ring and are provided with a transparent contact body, which is placed onto the cornea of an eye to be treated.

The light projector 60 is movable relative to the light source 2 in such a way that the length of the light-transmission path L from the light source 2 to the light projector 60 is changeable, as indicated by the arrow $\Delta x$ in FIGS. 1 to 8. Depending on the embodiment variant, the light projector 60 is fixedly attached in the application head 6 and is moved together with the application head 6 relative to the light source 2, as illustrated in, for example, FIGS. 1, 3, and 5 to 8, or the light projector 60 is embodied in a movable fashion in the application head 6 and is moved relative to the application head 6 and relative to the light source 2 within the application head 6, as illustrated in, for example, FIGS. 2 and 4.

The ophthalmic device 1 moreover comprises an interferometric measurement system 3 for measuring eye structures (e.g. front and rear surface of the cornea, front and rear surface of the lens, the retina, etc.) in the eye tissue 7. The interferometric measurement system 3 is configured for optical coherence tomography (OCT) with depth scanning. As illustrated schematically in FIGS. 1 to 9, the interferometric measurement system 3 comprises a light source 34, a measurement arm 30a, a reference arm 30b, a beam splitter 51 and a detector 31. The beam splitter 51 is provided for feeding the light beam, generated by the light source 34, firstly to the measurement arm 30a and secondly to the reference arm 30b. The beam splitter 51 moreover feeds to the detector 31 the light beams reflected by the eye structures in the eye tissue 7 and received by the measurement arm 30a and the light beam reflected by the mirror 32 of the reference arm 30b and received by the reference arm 30b. The detector 31 is configured to detect the interferences between the reflected measurement beam from the measurement arm 30a and the reflected reference beam from the reference arm 30b for determining and measuring the eye structures in the eye tissue 7. As shown schematically in FIGS. 1 to 9, the measurement arm 30a from the beam splitter 51 to the eye structures of the eye tissue 7 to be measured has a single path length m and the reference arm 30b has a single path length r from the beam splitter 51 to the mirror 32 (total length of the light-transmission path, including outward and return path, of the measurement arm 30a and of the reference arm 30b is 2m and 2r, respectively). As indicated by the arrow Δr, the mirror 32 of the reference arm 30b has a movable design in one embodiment variant such that the length of the reference arm 30b is changeable.

By way of example, the interferometric measurement system 3 is embodied as a time domain OCT (TD-OCT) with a changeable reference arm length, broadband light source 34 and detector 31 with simple but highly sensitive diode. The change in the reference arm length and different suitable methods for signal processing are described in e.g. EP0581871.

In another embodiment variant, the interferometric measurement system 3 is embodied without changeable reference arm length for static depth scanning. In one embodiment variant, the interferometric measurement system 3 is embodied as a so-called swept source OCT (SS-OCT) and comprises a light source 34 with changeable wavelength and a detector 31 with a simple but highly sensitive photodiode.

In another variant, the interferometric measurement system 3 is embodied as a spectral domain OCT (SD-OCT) with broadband light source 34 and suitable detector 31 (e.g. diffraction grating with CCD line).

In the following paragraphs various embodiment variants of the ophthalmic device 1, with different embodiments of the interferometric measurement system 3 and different arrangements of the components of the interferometric measurement system 3, are described with reference to FIGS. 1 to 8. It is noted here that the aforementioned embodiment variants, in particular the movability of the light projector 60 with or relative to the application head 6, the movably or rigidly embodied arm 4 and the embodiment with or without attachment means 61, are combinable with the following embodiment variants of the interferometric measurement system 3, even if not all combinations are explicitly illustrated in one of FIGS. 1 to 8.

In the embodiment variants in FIGS. 1 to 7, the interferometric measurement system 3 is coupled into the light-transmission path L from the light source 2 to the light projector 60, which is provided for the treatment of the eye tissue 7 by means of laser pulses. In these optically coupled-in embodiment variants of the interferometric measurement system 3, provision is respectively made in the ophthalmic device 1 for an optical element, which is movable in relation to the light source 2 and which prevents the path length difference (m−r or 2(m−r)) between measurement arm 30a and reference arm 30b from changing as a result of a change in length Δx of the light-transmission path L caused by the movement of the light projector 60.

Figure 2:
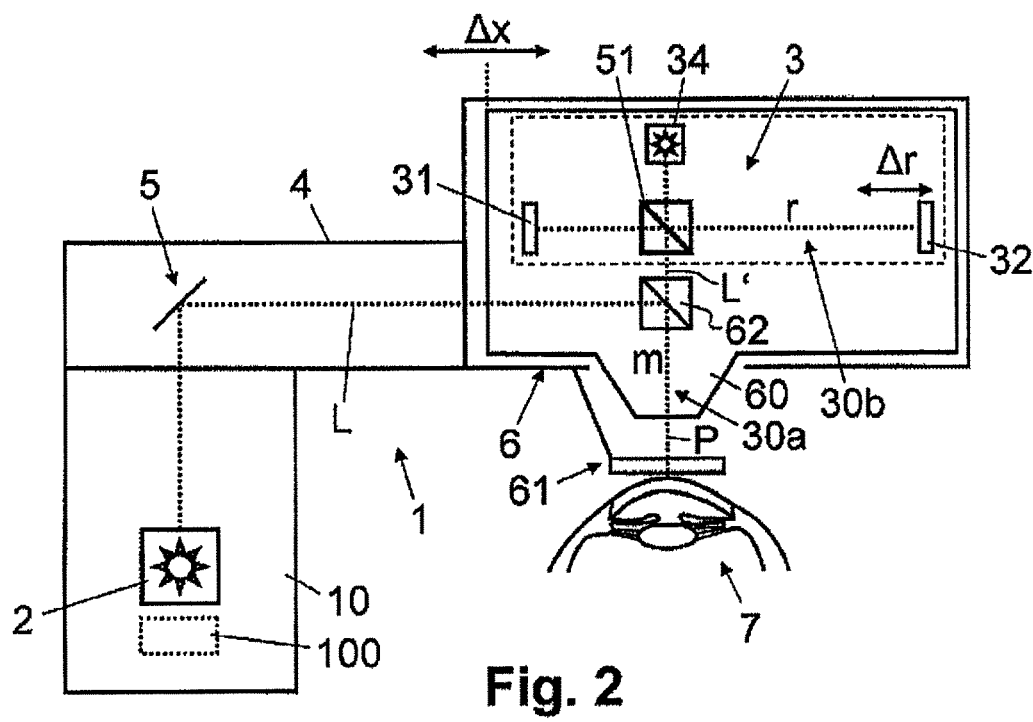
FIG. 2: schematically shows a cross section of an ophthalmic device for treating eye tissue by means of laser pulses, which has an interferometric measurement system for measuring eye structures, which measurement system is fixedly connected to a movable light projector.
Figure 3:
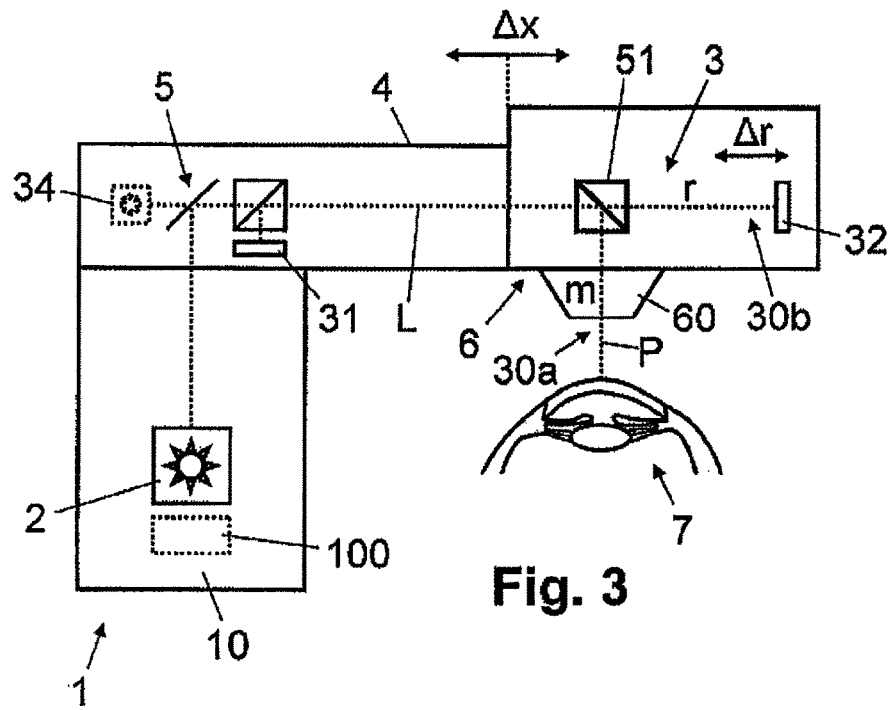
FIG. 3: schematically shows a cross section of an ophthalmic device for treating eye tissue by means of laser pulses, which has an interferometric measurement system for measuring eye structures, the reference arm of which measurement system is arranged in a movable application head.
Figure 4:
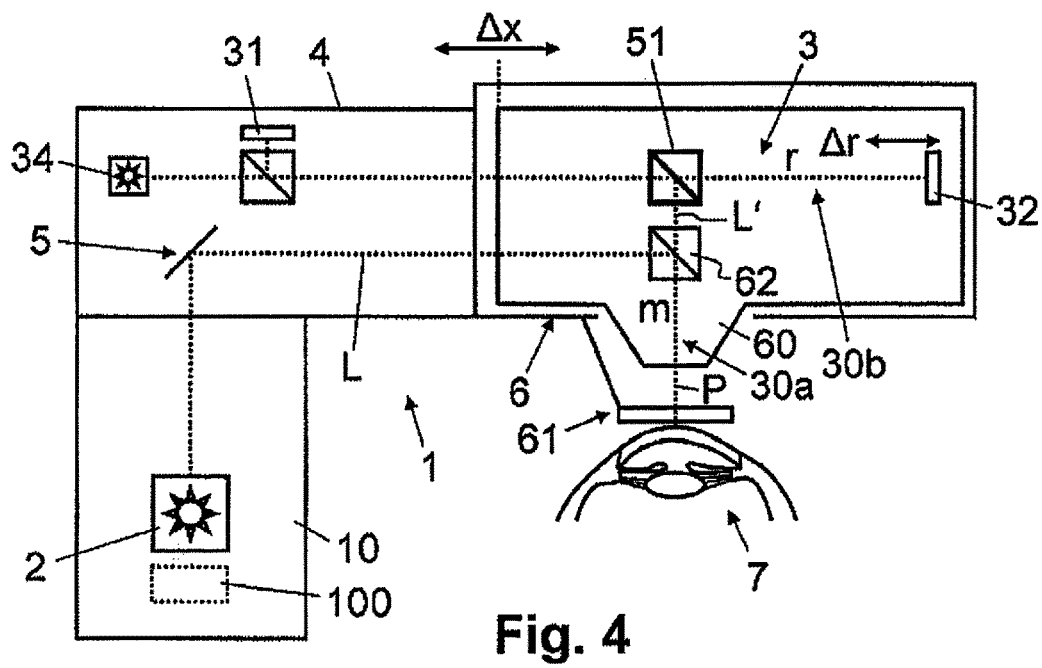
FIG. 4: schematically shows a cross section of an ophthalmic device for treating eye tissue by means of laser pulses, which has an interferometric measurement system for measuring eye structures, the reference arm of which measurement system is fixedly connected to a movable light projector.

In the embodiment variants of FIGS. 1 to 4, the movable optical element is a beam splitter 51, which is fixedly connected to the light projector 60 and by means of which the measurement arm 30a and the reference arm 30b of the interferometric measurement system 3 are coupled. As can be seen from FIGS. 1 to 4, the reference arm 30b of the interferometric measurement system 3 is arranged in the application head 6 in these variants and is moved together with the light projector 60 and the beam splitter 51 connected thereto—together with the application head 6 (FIGS. 1 and 3) or relative to the application head 6 within the application head 6 (FIGS. 2 and 4). In the embodiment variants of FIGS. 1 and 2, the detector 31 of the interferometric measurement system 3 is also arranged in the application head 6 and is moved together with the application head 6 (FIG. 1) or relative to the application head 6 within the application head 6 (FIG. 2). In the embodiment variants of FIGS. 3 and 4, the detector 31 of the interferometric measurement system 3 is arranged outside of the application head 6, for example in the arm 4 or in the base station 10.

Figure 5:
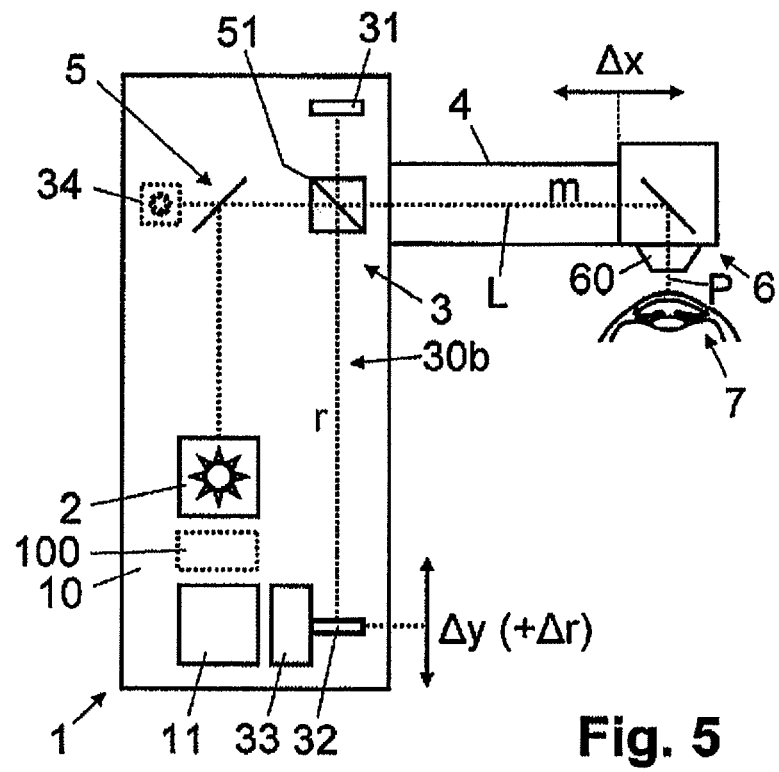
FIGS. 5 and 6: respectively schematically show a cross section of an ophthalmic device for treating eye tissue by means of laser pulses, which has an interferometric measurement system for measuring eye structures, the reference arm of which measurement system has a changeable length and is arranged in a base station.
Figure 6:
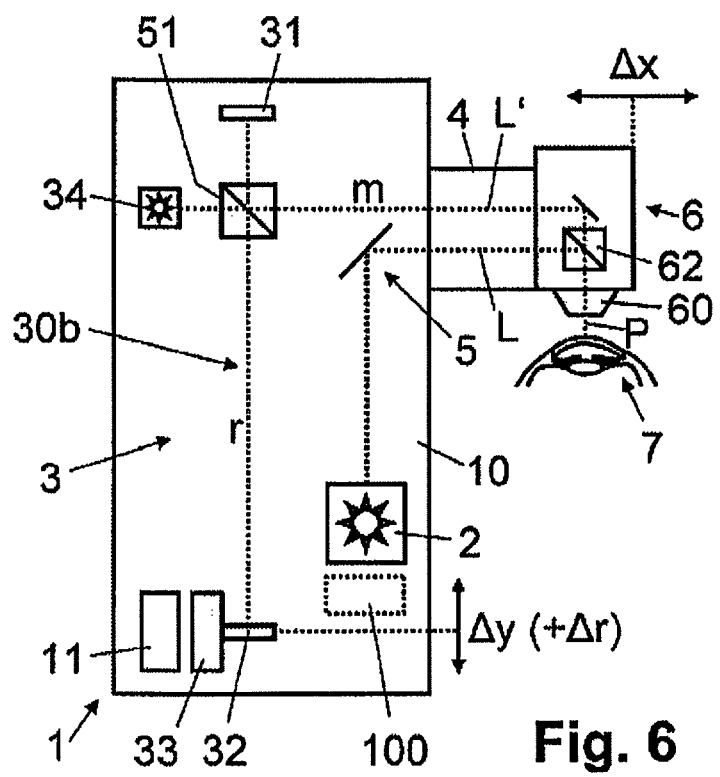

In various embodiment variants, the interferometric measurement system 3 is directly coupled into the light-transmission path L from the light source 2 to the light projector 60 by means of the beam splitter 51 (e.g. in FIGS. 1, 3 and 5) or the interferometric measurement system 3 is coupled into the light-transmission path L by means of a further beam splitter 62, which is connected to the beam splitter 51 of the interferometric measurement system 3 via a separate light-transmission path L' (e.g. FIGS. 2, 4 and 6).

In the embodiment variants of FIGS. 1 to 4, the light source 34 of the interferometric measurement system 3 is, depending on the variant, arranged in the application head 6 (e.g. FIG. 1 or 2) or in the arm 4 or in the base station 10 (e.g. FIG. 1, 3 or 4). In alternative embodiment variants, the light source 2 also serves as light source for the interferometric measurement system 3 (e.g. FIG. 1 or 3).

In the embodiment variants of FIGS. 5 and 6, the movable optical element is a mirror 32 arranged in the reference arm 30b, which mirror is moved to compensate a movement Δx of the light projector 60, as indicated by the arrow Δy (Δy=kΔx, where k is a system constant), in such a way that a change in the path length difference (m−r) of measurement arm 30a and reference arm 30b, caused by the movement Δx of the light projector 60, is prevented. To this end, the ophthalmic device 1 comprises a control module 11 and a movement driver 33, coupled to the mirror 32 of the reference arm 30b, which are configured to displace the mirror 32 in such a way that the path length r of the reference arm 30b is adapted in accordance with the change Δx in the length of the light-transmission path L caused by the movement of the light projector 60. By way of example, the control module 11 is configured as a programmed software module for controlling a processor of the ophthalmic device 1 or as a logic module, embodied as a piece of hardware.

Moreover, all embodiment variants can be combined with additional beam splitters, optically imaging elements and optical fibres. In particular, the interferometric measurement system 3 can be coupled into the light-transmission path L by optical fibres. By way of example, in a sub-variant of the embodiment variant as per FIG. 5, the interferometric measurement system 3 is coupled into the light-transmission path L by an optical fibre and a beam-splitting mirror in an arm 4 embodied as articulated arm. In a sub-variant of the embodiment variant as per FIG. 6, the interferometric measurement system is, in another example, likewise coupled into the light-transmission path L' by an optical fibre.

Figure 7:
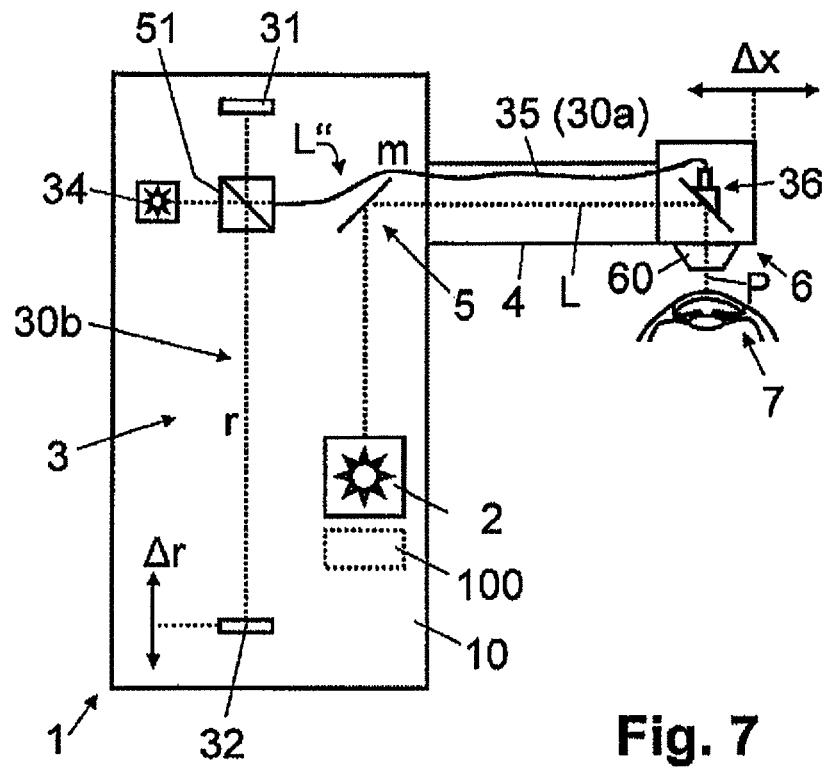
FIGS. 7 and 8: respectively schematically show a cross section of an ophthalmic device for treating eye tissue by means of laser pulses, which has an interferometric measurement system for measuring eye structures, with a flexible optical fibre in the measurement arm.

In the embodiment variant of FIG. 7, the movable optical element is an optical waveguide coupling 36, which is fixedly connected to the light projector 60 and incorporates the light projector 60 into the interferometric measurement system 3 via a flexible optical fibre 35. The flexible optical fibre 35 forms a light-transmission path L", which is separate from the light-transmission path L from the light source 2 to the light projector 60 and by means of which the beam splitter 51 of the interferometric measurement system 3 is connected to the light projector 60. The length of the optical fibre 35 or of the separate light-transmission path L" from the beam splitter 51 of the interferometric measurement system 3 to the light projector 60 remains constant independently of a change in length, caused by a the movement Δx of the light projector 60, of the light-transmission path L from the light source 2 to the light projector 60. Hence the path length difference (m−r) between measurement arm 30*a* and reference arm 30*b* remains unchanged.

Figure 8:
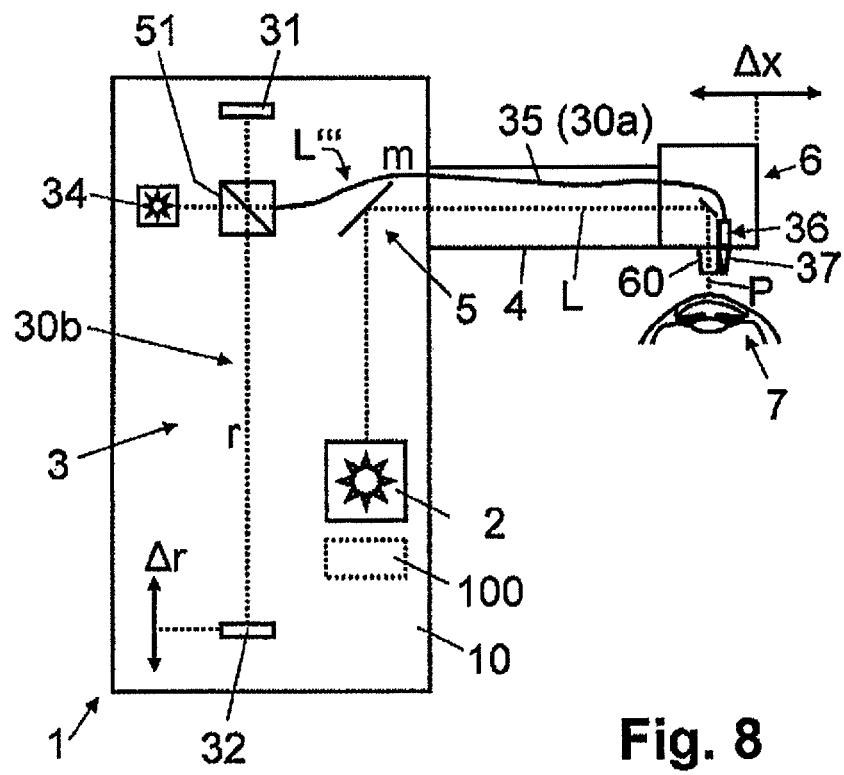
Figure 9:
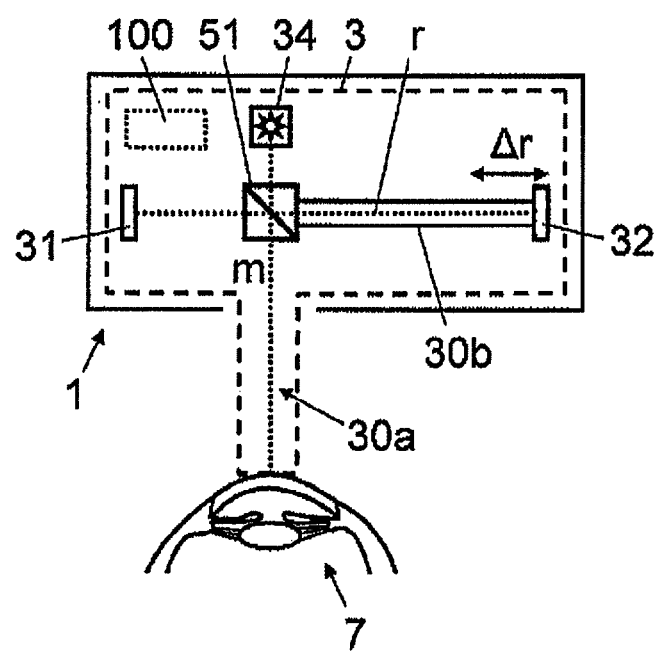
FIG. 9: schematically shows a cross section of an ophthalmic device for treating eye tissue by means of laser pulses, which has an interferometric measurement system with light source, detector, measurement arm and reference arm for measuring eye structures.

In the embodiment variant as per FIG. 8, a further light projector 37, which serves to project the measurement beam of the interferometric measurement system 3 in the measurement arm 30*a*, is provided in addition to the light projector 60 provided for the focused projection of the laser pulses P into the eye tissue 7. This additional light projector 37 is fixedly connected to the light projector 60 and therefore also moved by the movements of the latter. In the embodiment variant of FIG. 8, provision is made for an optical waveguide coupling 36 as further movable optical element, which is fixedly connected to the light projectors 60 and 37 and which incorporates the additional light projector 37—as was described above in conjunction with FIG. 7—into the interferometric measurement system 3 via the flexible optical fibre 35. The flexible optical fibre 35 forms a light-transmission path L''', which is separate from the light-transmission path L from the light source 2 to the light projector 60 and by means of which the beam splitter 51 of the interferometric measurement system 3 is connected to the additional light projector 37 such that, in this case too, the path length difference (m−r) between measurement arm 30*a* and reference arm 30*b* remains unchanged in the case of movements Δx of the light projector 60 in relation to the light source 2.

Finally, it should be noted that the ophthalmic device 1 is provided with an additional correction module 100 in one embodiment variant, which correction module is configured for the numerical correction of remaining errors, which may remain in practice even if the above-described correction or compensation measures are used for preventing changes in the path length difference (m−r) between measurement arm 30*a* and reference arm 30*b* in the case of movements Δx of the light projector 60 in relation to the light source 2, for example as a result of closed-loop control deviations or in the case of step-wise displacement of the reference arm 30*b*. By way of example, the correction module 100 is configured as a programmed software module for controlling a processor of the ophthalmic device 1 or as a logic module, embodied as a piece of hardware. In one variant, the correction module 100 is configured to carry out the correction or compensation of changes in the path length difference (m−r) between measurement arm 30*a* and reference arm 30*b* emerging in the case of movements Δx of the light projector 60 in relation to the light source 2 in a completely numerical fashion, for example as an alternative to the above-described correction or compensation measures or as a backup solution in the case of a malfunction of the control module 11 or of the movement driver 33. The correction module 100 is configured to carry out the correction of changes in the path length difference (m−r) on the basis of the measurement or image data of the eye structures captured by the interferometric measurement system 3, for example by detecting and removing jumps and displacements in the contour profile of the eye structures. The captured contours of the eye structures are, for example, imaged as lines by means of pixels in an array and changes in the path length difference (m−r) on the basis of jumps and displacements are determined, which are detected, for example by means of suitable image processing algorithms, over a plurality of lines—i.e. over the contour profiles of a plurality of eye structures arranged at different depths in the eye tissue.

The invention claimed is:

1. Ophthalmic device for treating eye tissue by means of laser pulses, comprising:
   a base station,
   a first light source arranged in the base station and configured to generate the laser pulses,
   a light projector for focused projection of the laser pulses into the eye tissue, wherein the light projector is movable in relation to the first light source in such a way that a length of a light-transmission path from the first light source to the light projector is changeable, wherein the light projector is connected to the base station via an arm,
   an interferometric measurement system configured to measure eye structures,
   a reflecting optical element, which is movable in relation to the first light source and provided for preventing a change in a path length difference, between a measurement arm and a reference arm of the interferometric measurement system, as a result of a change in the length of the light-transmission path, caused by a movement of the light projector, wherein the reflecting optical element is arranged in the reference arm, and wherein the reflecting optical element is arranged in the base station, and
   a control module and a movement driver, which are configured to displace the reflecting optical element in the base station, for compensating the movement of the light projector, in such a way that a path length of the reference arm is adapted in accordance with the change in the length of the light-transmission path caused by the movement of the light projector.

2. Ophthalmic device of claim 1, wherein the interferometric measurement system is coupled into said light-transmission path.

3. Ophthalmic device of claim 1, wherein the reflecting optical element is an optical waveguide coupling, which is fixedly connected to the light projector and which incorporates the light projector into the interferometric measurement system by means of a flexible optical fibre.

4. Ophthalmic device of claim 1, comprising a further light projector, which is fixedly connected to the light projector and which is incorporated into the interferometric measurement system by means of a flexible optical fibre.

5. Ophthalmic device of claim 1, wherein the reflecting optical element is a beam splitter, which is fixedly connected to the light projector and by means of which the measurement arm and the reference arm of the interferometric measurement system are coupled.

6. Ophthalmic device of claim 1, wherein the ophthalmic device comprise an application head which is configured to be applied onto the eye tissue and the light projector is arranged in the application head.

7. Ophthalmic device of claim 6, wherein the reference arm of the interferometric measurement system is arranged in the application head.

8. Ophthalmic device of claim 6, wherein the interferometric measurement system comprises a light source, which is arranged in the application head.

9. Ophthalmic device of claim 6, wherein the interferometric measurement system comprises a detector, which is arranged in the application head.

10. Ophthalmic device of claim 6, wherein the interferometric measurement system comprises a detector, which is arranged outside of the application head.

11. Ophthalmic device according to of claim 1, wherein the interferometric measurement system comprises a second light source which is arranged in the base station, wherein the second light source is different from the first light source, and wherein the interferometric measurement system comprises a detector which is arranged in the base station.

12. Ophthalmic device of claim 1, wherein the interferometric measurement system has a reference arm with a changeable reference arm length.

* * * * *